United States Patent [19]

Mueller et al.

[11] 4,202,939
[45] May 13, 1980

[54] GLUCOAMYLASE IMMOBILIZED ON CATIONIC COLLOIDAL SILICA

[75] Inventors: Nancy J. Mueller, Lyons; Dennis J. Holik, Naperville, both of Ill.

[73] Assignee: CPC International Inc., Englewood Cliffs, N.J.

[21] Appl. No.: 829,690

[22] Filed: Sep. 1, 1977

[51] Int. Cl.$^2$ .................. C12D 13/04; C07G 7/02
[52] U.S. Cl. ........................ 435/96; 435/177; 435/205
[58] Field of Search ......... 195/31 R, 63, 68, DIG. 11; 435/176, 205, 96

[56] References Cited

U.S. PATENT DOCUMENTS

| | | | |
|---|---|---|---|
| 3,556,945 | 1/1971 | Messing | 195/63 |
| 3,796,634 | 3/1974 | Haynes et al. | 195/63 |
| 3,802,997 | 4/1974 | Messing | 195/63 X |
| 4,011,137 | 3/1977 | Thompson et al. | 195/63 X |
| 4,132,595 | 1/1979 | Hebeda et al. | 195/31 R |
| 4,144,127 | 3/1979 | Enokizono et al. | 195/31 F X |

OTHER PUBLICATIONS

Properties, Uses, Storage and Handling LUDOX Colloidal Silica, E. I. Du Pont de Nemours & Co., Inc., Wilmington, Del., 10/1975 (pp. 1-20).

*Primary Examiner*—David M. Naff
*Attorney, Agent, or Firm*—Stanley M. Parmerter

[57] ABSTRACT

A process for production of dextrose from starch wherein a starch hydrolyzate produced using soluble α-amylase or a combination of soluble glucoamylase and α-amylase is treated with glucoamylase immobilized on a cationic colloidal silica to produce a dextrose-containing syrup.

8 Claims, No Drawings

GLUCOAMYLASE IMMOBILIZED ON CATIONIC COLLOIDAL SILICA

FIELD OF INVENTION

This invention relates to the production of dextrose through the use of an immobilized glucoamylase enzyme.

BACKGROUND OF INVENTION

Starch is a polymeric carbohydrate of very high molecular weight. Its monomeric units, termed anhydroglucose units, are derived from dextrose, and the complete hydrolysis of starch yields dextrose. In the United States, dextrose is manufactured from corn starch; in Europe from corn starch and potato starch; and in Japan from corn starch and white sweet potato starch.

Until 1960, dextrose was prepared from starch by acid hydrolysis. The method of preparation involved heating starch with hydrochloric or sulfuric acid at temperatures of 120°–145° C., then neutralizing the hydrolysis mixture with sodium carbonate, clarifying, and crystallizing the dextrose. Unfortunately, the yield of dextrose is lowered by the formation of relatively large amounts of reversion products, i.e., products which are formed by the recombination of dextrose molecules. Also, because of the high temperature and low pH of the hydrolysis reaction, some of the dextrose produced is converted to hydroxymethylfurfural, levulinic acid and color bodies. The formation of such degradation products is irreversible and, to the extent they are formed, the yield of desired dextrose is, of course, adversely affected. Still further, the use of hydrochloric acid or in some instances, sulfuric acid, and the subsequent neutralization of this acid with alkali results in the formation of inorganic salts which interfere with crystallization of the final dextrose product.

Later, hydrolysis of starch to dextrose was accomplished by means of enzymes. The principal enzyme used for such purposes was, and continues to be, glucoamylase. This enzyme effectively hydrolyzes the starch by cleaving one molecule of dextrose at a time from the starch molecule. As a practical matter, however, it is necessary first to thin the starch before subjecting it to the action of glucoamylase. This thinning step may be accomplished either by means of acid or enzyme. The starch is thinned to a D.E. of about 10–20, then treated with glucoamylase. This two-stage process is referred to as an acid-enzyme process or an enzyme-enzyme process, depending upon the nature of the thinning step employed.

In the acid-enzyme process, starch is liquefied and hydrolyzed in an aqueous suspension containing 20 to 40 percent starch and an acid, such as hydrochloric acid. The suspension is then heated to a high temperature, i.e., a temperature between about 70° C. and about 160° C. and at a pH between about 1 and 4.5 to liquefy and partially hydrolyze the starch. Typical acid-enzyme processes are disclosed in U.S. Pat. Nos. 2,305,168; 2,531,999; 2,893,921; 3,021,944; and 3,042,584.

In the enzyme-enzyme process, starch is liquefied and partially hydrolyzed in an aqueous suspension containing 20 to 40 percent starch and a liquefying enzyme, such as bacterial α-amylase enzyme at a temperature of from about 85° C. to about 105° C. The dextrose equivalent of the liquefied and partially hydrolyzed starch is generally less than about 20 and preferably less than about 10. The mixture is then subjected to a temperature above about 95° C. and preferably between 110° C. and 150° C. to insure complete starch solution. The starch hydrolyzate is then cooled to a temperature of less than 95° C. and subjected to further treatment with bacterial α-amylase to hydrolyze the starch to a D.E. of up to about 20. This process is disclosed and claimed in U.S. Pat. No. 3,853,706.

By either process the digested starch may thereafter be converted to dextrose or dextrose-containing syrups by other enzymes such as glucoamylase. Glucoamylase preparations are produced from certain fungi strains such as those of the genus Aspergillus; for example, *Aspergillus phoenicis, Aspergillus niger, Aspergillus awamori*, and certain strains from the Rhizopus species and certain Endomyces species. Glucoamylase effects the hydrolysis of starch proceeding from the non-reducing end of the starch molecule to split off single glucose units at the alpha-1,4 linkages or at the alpha-1,6 branch points. Commercial glucoamylase enzyme preparations comprise several enzymes in addition to the predominating glucoamylase; for example, small amounts of proteases, cellulases, α-amylases, and transglucosidases.

Considerable interest has developed in the use of immobilized enzyme technology for production of dextrose from starch. Immobilization may increase enzyme stability, the enzyme material may be re-used repeatedly, and a more precise control of the reaction is possible. Various procedures have been described for the immobilization of glucoamylase.

References which review the art of enzyme immobilization, with particular attention to the immobilization of glucoamylase are given in U.S. Pat. No. 4,011,137.

Processes for the immobilization of enzymes on colloidal silica have recently been reported. U.S. Pat. No. 3,802,997 disclosed that "colloidal silica could be used to bind enzymes." However, this patent taught that it is necessary to combine a substrate of the enzyme with the carrier before the enzyme is bound to the carrier. The process included an expensive freeze drying or spray drying step to isolate the product. In U.S. Pat. No. 3,796,634, colloidal silica was also used as a carrier for enzymes. In this case, glutaraldehyde was used to cross-link the enzyme and chemically bind it to the silica. Alternatively, polyethyleneimine was first bound to the silica and then the enzyme was attached to the polyamine on the silica surface by means of a cross-linking agent. Very finely divided particles were obtained by the methods described in both of these patents. Such small enzyme-containing particles are difficult to remove from batch reactions and produce unmanageable pressure drops when attempts are made to use them in column operation.

In a pending U.S. application, Ser. No. 780,374, filed Mar. 23, 1977 now U.S. Pat. No. 4,144,127, a glucose isomerase enzyme was bound to colloidal silica. Binding of the enzyme was improved by the use of glutaraldehyde and the particle size was increased by freezing the mixture and thawing it at least two times. This produced granules or flakes having a particle size of 20–100 mesh which were large enough for good flow in a column isomerization reaction. No examples of the binding of glucoamylase were given in any of these patents.

It has been discovered that the small particles of cationic colloidal silica can be agglomerated to larger particles if they are gelled by raising the pH to about 6.5, then frozen and thawed. It has been discovered furthermore, that when the colloidal silica is agglomerated by this method in the presence of glucoamylase, the enzyme is immobilized in an active form. No crosslinking agent is necessary to bind the enzyme to the silica, and the enzyme does not leach out when the particles are suspended in or washed with aqueous solutions.

In contrast, if the colloidal silica is first agglomerated and the resulting particles are then contacted with the enzyme, very little of the enzyme is bound to the silica.

An important advantage of this enzyme composite is that it is relatively noncompressible. For example, it undergoes no volume change when spun in a centrifuge at 2000 rpm for 15 minutes. This noncompressibility, coupled with good particle size makes the enzyme composite very suitable for carrying out enzymatic conversions in fixed bed reactors with a minimum of pressure drop across the reaction zone. These properties of the composite also make it useful for enzymatic conversions in expanded bed (upflow) reactors, continuous stirred tank reactors and batch reactors.

SUMMARY OF THE INVENTION

In accordance with this invention, a process is provided for the production of an insoluble, active enzyme which comprises:
(a) contacting an enzyme solution with cationic colloidal silica,
(b) converting the mixture to a gel by raising the pH to about 6.5,
(c) freezing the gel by holding it below about $-15°$ C. for about 24 hours,
(d) thawing the frozen solid by allowing it to stand at about 20° C., and
(e) separating the resulting solid enzyme-containing particles.

In another embodiment, the present invention is directed to a process for producing dextrose or dextrose-containing syrups from a starch hydrolyzate which comprises the steps of:
(a) treating a starch hydrolyzate at a pH between about 4.0 and 4.5 with an immobilized enzyme composite consisting of a starch hydrolyzing enzyme, and
(b) recovering the dextrose product.

DESCRIPTION OF PREFERRED EMBODIMENTS

The colloidal silica used in this invention is an aqueous colloidal dispersion of silica particles. Such products are available from the DuPont Company under the trade name LUDOX. Most of the LUDOX products have negatively charged particles. However, the preferred LUDOX is LUDOX-130M which has positively charged colloidal particles. Although colloidal silicas on the market have a particle size in the range of 7–24 nanometers in diameter, colloidal silicas can be used in this invention in any form, regardless of the particle size.

The glucoamylase used in this invention can be any of the well-known fungal amylase preparations, particularly those derived from members of the Aspergillus genus, the Endomyces genus or the Rhizopus genus. A particularly preferred glucoamylase is that available from the process described in U.S. Pat. No. 3,042,584 (Kooi, et al.) whereby a fungal amylase preparation is freed of undesired transglucosidase activity by treatment in an aqueous medium with a clay material.

Glucoamylase activity units are determined as follows:

The substrate is a 10–20 D.E. α-amylase thinned hydrolyzate of waxy maize starch dissolved in water and diluted to 4.0 grams of dry substance per 100 ml of solution. Exactly 50 ml of the solution is pipetted into a 100 ml volumetric flask. To the flask is added 5.0 ml of 1.0 molar sodium acetate-acetic acid buffer (pH 4.3). The flask is placed in a water bath at 60° C. and after 10 minutes the proper amount of enzyme preparation is added. At exactly 120 minutes after addition of the enzyme preparation, the solution is adjusted to a phenolphthalein end-point with 0.5 N sodium hydroxide. The solution is then cooled to room temperature and diluted to volume. A reducing sugar value, calculated as dextrose, is determined on the diluted sample and on a control with no enzyme preparation added. Glucoamylase activity is calculated as follows:

$$A = (S-B)/(2 \times E)$$

where:
A = Glucoamylase activity units per ml (or per gram) of enzyme preparation.
S = Reducing sugars in enzyme converted sample, grams per 100 ml.
B = Reducing sugars in control, grams per 100 ml.
E = Amount of enzyme preparation used, ml (or grams).
S should not exceed 1.0 grams per 100 ml.

The starch hydrolyzate used as starting material can be prepared either by an acid liquefaction or by an enzyme liquefaction conversion process as previously described.

According to this invention, the starch hydrolyzate is treated solely with an immobilized glucoamylase preparation to produce the dextrose. Treatment may be either in a batch or in a column.

The term dextrose equivalent or D.E. value used herein refers to the reducing sugars content of the dissolved solids in a starch hydrolyzate expressed as percent dextrose as measured by the Schoorl method (Encyclopedia of Industrial Chemical Analysis, Vol. 11, pp 41–42).

Dextrose syrups were analyzed using high pressure liquid chromatography. Components were chromatographed by elution with water from a cation exchange resin in the calcium form. Eluted components were detected by means of a differential refractometer. Non-dextrose carbohydrates were quantitated using an electronic integrator, and dextrose was obtained by difference. The general procedure is that given in "Analysis of Carbohydrate Mixtures by Liquid Chromatography," *Am. Soc. Brew. Chem. Proc.*, 1973, pp 43–46. The resin used was Aminex Q 15-S in the calcium form, Bio-Rad. Laboratories, Richmond, Calif.

The enzyme to be contacted with the colloidal silica is used in solution after proper dilution with water. Dilution may also be made with a solution of a salt that stabilizes the enzyme or with a solution of a buffer which maintains the pH. In the case of glucoamylase, the preferred concentrations are 5 to 200 units per ml. The colloidal silica is used as such, or preferably after proper dilution with water to a concentration of 10 to 30% by weight.

Any enzyme can be used in this process which will retain its activity after insolubilization. The preferred enzymes are those carbohydrases such as glucoamylase, pullulanase, alpha-amylases, beta-amylases, and isoamylase.

The colloidal silica is gelled in the presence of the enzyme by the adjustment of pH. This may be accomplished with dilute acids, or dilute alkalies, or with acidic or basic salts. In the case of glucoamylase and cationic colloidal silica, it was found that adjustment of pH with dilute sodium carbonate solution was preferable to the adjustment of pH with dilute sodium hydroxide solution. The optimum pH for the gelation is governed by the stability and properties of the enzyme used.

The gelled mixture may be stabilized by the addition of cross-linking agents such as glutaraldehyde. Surprisingly, in the case of glucoamylase and cationic colloidal silica, better results were obtained without the use of such a cross-linking agent.

The gel is frozen at any convenient temperature below the freezing point of the mixture, preferably in the range of −15° to −20° C. Time of cooling will vary with the temperature, volume of material to be frozen and other cooling conditions. The mixture should be held below the freezing point long enough so that the mixture is completely frozen.

The frozen mixture is allowed to thaw slowly, usually in a room at 15° C. to 25° C. However, any temperature may be employed which does not cause inactivation of the enzyme.

The process conditions for gelatinization and freezing and thawing of the enzyme mixture are adjusted to give particles which retain enzyme activity and which have sufficient size and structure to permit flow of a syrup through a column packed with the particles or to permit easy recovery of the particles from a batch reaction by filtration or centrifugation. In addition, the structure of the enzyme-containing particles should be such as to permit substrate diffusion so that enzymatic reaction occurs. The desired particle size and structure is achieved by adjusting the initial concentration of the colloidal silica, by gelation and freezing in the presence of salts with or without substrate, and by the rate of freezing and thawing.

The immobilized enzyme composite of this invention is contacted with a starch hydrolyzate at such a temperature as to give a practical rate of reaction without causing an impractical loss of enzyme activity. With glucoamylase, the useful temperature range is 20° C. to 70° C. and the preferable temperature range is 40° C. to 50° C.

It is possible to use a wide range of hydrolyzate concentrations in the practice of this invention. They may range from 5 to 60% solids; however, substrates with low D.E. may be too viscous for use at the higher solids concentration.

The pH of the substrate may vary from 3.5 to 7.0, with the optimum pH varying with the enzyme used. With glucoamylase, the preferred pH range is 4.2 to 4.5.

The process of this invention using an immobilized glucoamylase composite may be used to produce syrups in which a high percentage of the carbohydrate is dextrose. The percentage of dextrose in the product may be adjusted by varying the contact time between the hydrolyzate and the enzyme, the temperature, the concentration of the hydrolyzate used, and the composition of the hydrolyzate used. It is thus possible to produce syrups with controlled amounts of dextrose as well as those with high amounts of dextrose.

The process of this invention may also be used to produce syrups in which varying percentages of the carbohydrate is maltose. This is achieved by using an immobilized β-amylase composite in place of the immobilized glucoamylase composite.

The invention is further illustrated by reference to the following examples, in which all parts and percentages are by weight unless otherwise noted.

EXAMPLE 1

To 5 ml of a 30% dispersion of cationic colloidal silica (LUDOX 130M) was added 4 ml of water and a solution of 112 units of glucoamylase in 2 ml of water. The resulting suspension, pH 4.4, was shaken for 15 minutes at room temperature. Then 0.045 ml of a 25% solution of glutaraldehyde was added. The pH was adjusted to 6.5 by the addition of 0.1 N sodium hydroxide solution. A gel formed as the mixture was shaken for 20 minutes at room temperature. The gel was frozen for 24 hours at −20° C. When the frozen material was brought to room temperature and left for 3 hours without stirring, solid and liquid phases separated. The solid was collected by suction filtration and washed with 135 ml of water.

Assay of the combined filtrate and washings showed that no active enzyme was present. Immobilized enzyme showed bound glucoamylase activity. An aqueous suspension of the solid was examined under the microscope. The transparent platelets varied in diameter from 1 to 380μ. Most of the particles were 100μ to 150μ in diameter.

EXAMPLE 2

The procedure of Example 1 was repeated using three times the quantities of all materials. Glucoamylase activity was 14 units per gram.

EXAMPLE 3

The procedure of Example 2 was repeated except that no glutaraldehyde was added. Seventeen units of glucoamylase per gram of dry solid was bound in an active form.

This indicates that with cationic colloidal silica more glucoamylase is bound in the active form when no glutaraldehyde is used as a cross-linking agent.

EXAMPLE 4

The procedure of Example 3 was repeated except that the pH was adjusted to 6.5 with 1% sodium carbonate solution instead of 0.1 N sodium hydroxide solution. Bound activity was 24 units of glucoamylase per gram of dry solid.

EXAMPLE 5

This example shows that cationic colloidal silica particles preformed by gelation and freezing bind an insignificant amount of glucoamylase.

To a mixture of 15 ml of 30% cationic colloidal silica (LUDOX 130M) and 10 ml of water, was added slowly with shaking, 10 ml of 1% sodium carbonate solution. This raised the pH of the mixture to 6.5. The white gel was frozen at −20° C. for 24 hours. The mixture was left for 2 hours at room temperature before the solid was collected by suction filtration and washed with water.

A 2-g sample of the solid was shaken for one hour with 50 ml of 0.05 molar sodium acetate buffer pH 4.3 to 4.5. The solid was removed by filtration and washed with additional sodium acetate buffer at pH 4.3. To the solid was added a solution of 150 units of glucoamylase in 15 ml of 0.04 molar sodium acetate buffer and the pH was adjusted to 4.3 with acetic acid. The mixture was shaken overnight at room temperature. The solid was collected and washed with 200 ml of water. Analysis showed 139 units of glucoamylase remained unbound. Bound activity was 2 units per gram.

EXAMPLE 6

To a mixture of 180 ml of a 30% by weight solution of cationic colloidal silica (LUDOX 130M) and 120 ml of distilled water, was added with shaking, 60 ml of a solution containing 3990 units of glucoamylase. The mixture was shaken for 15 minutes at room temperature. Then 140 ml of a 1% solution of sodium carbonate was added dropwise with shaking over a period of 2 hours. The thick white gel was placed in a freezer at −20° C. for 24 hours.

The material was then left at room temperature for 5 hours to thaw. The solid was collected and washed with 400 ml of distilled water. It was then transferred to a beaker and washed four times with water by decantation to remove fine particles. Sixteen units of glucoamylase per gram of dry carrier were bound in active form.

EXAMPLE 7

To a glass column (inside diameter 30 mm, length 190 mm) was added 100 ml of the LUDOX 130M containing glucoamylase prepared as described in Example 6. A 25% aqueous solution of a 29 D.E. α-amylase thinned starch hydrolyzate was passed through the column at the rate of 0.5 bed volumes per hour (BVH). Hydrolyzate pH was adjusted to 4.3 and 0.025% propyl parasept was added to retard microbial growth. Temperature of the column was maintained at 45° C. by means of a water jacket. The carbohydrate composition of the syrup flowing from the column was determined by high pressure liquid chromatography. Average compositions were as follows:

Dextrose: 90.9±0.5%
Disaccharides: 2.2%
Trisaccharides: 0.6%
Tetra and Higher Saccharides: 6.3%

Saccharide composition of the effluent remained nearly constant for 8 days of operation. No active glucoamylase was detected in the effluent.

EXAMPLE 8

A 71 D.E. starch hydrolyzate, prepared from 29 D.E. starch hydrolyzate by digestion with soluble glucoamylase, was used as starting material in place of the 29 D.E. starch hydrolyzate used in Example 5. The column was run for 3 days at 45° C. and pH 4.3. Analysis of the carbohydrate product by high pressure liquid chromatography showed the following average values:

Dextrose: 93.1±0.4%
Disaccharides: 2.0%
Trisaccharides: 0.6%
Tetra and Higher Saccharides: 4.3%

After the column had been used continuously for 14 days, a sample of the insolubilized enzyme complex was removed from the column. It was found to contain 11 units of glucoamylase activity per gram.

These results show that glucoamylase immobilized by the procedure of this invention is capable of converting starch hydrolyzate to dextrose syrups and that it may be used for this purpose for sustained periods in continuous column operation.

While the invention has been described with specific embodiments thereof, it will be understood that it is capable of further modification and adaptations or variations as are apparent to those skilled in the enzyme and starch hydrolysis art.

I claim:

1. An insoluble active enzyme consisting essentially of a complex of a soluble starch hydrolyzing enzyme and an agglomerated cationic colloidal silica.

2. The complex of claim 1 wherein the enzyme is a glucoamylase.

3. A process for preparing an insoluble enzymatically active glucoamylase which comprises the steps of:
   (a) contacting a glucoamylase solution with cationic colloidal silica,
   (b) converting the mixture to a gel by raising the pH to about 6.5,
   (c) freezing the gel by holding it below about −15° C. for about 24 hours,
   (d) thawing the frozen solid by allowing it to stand at about 20° C., and
   (e) separating the resulting solid enzyme-containing particles.

4. A process for converting a starch hydrolyzate to a dextrose syrup which comprises:
   (a) treating a starch hydrolyzate with an immobilized enzyme composite, prepared by the process of claim 3, consisting of a starch hydrolyzing enzyme bound to an agglomerated cationic colloidal silica, and
   (b) recovering the dextrose product.

5. The process of claim 4 wherein the pH of the starch hydrolyzate is maintained between about 3.5 and 5.5.

6. The process of claim 4 wherein the pH of the starch hydrolyzate is maintained preferably between about 4.2 and 4.5.

7. The process of claim 4 wherein the starch hydrolyzate has a D.E. of between about 10 and 80.

8. The process of claim 4 wherein the starch hydrolyzing enzyme is glucoamylase.

* * * * *